United States Patent [19]

Py

[11] Patent Number: 4,792,334
[45] Date of Patent: Dec. 20, 1988

[54] OCCULAR TREATMENT APPARATUS

[76] Inventor: Daniel Py, 22 Ferncliff Terr., Short Hills, N.J. 07078

[21] Appl. No.: 118,388

[22] Filed: Nov. 6, 1987

[51] Int. Cl.$^4$ .............................................. A61H 33/04
[52] U.S. Cl. ..................................... 604/301; 604/295
[58] Field of Search ......................... 604/214, 295–302

[56] References Cited

U.S. PATENT DOCUMENTS

| | | | |
|---|---|---|---|
| 3,279,466 | 10/1966 | Mings | 604/302 |
| 4,085,750 | 4/1978 | Bosshold | 128/233 |
| 4,131,115 | 12/1978 | Peng | 128/249 |
| 4,386,608 | 6/1983 | Ehrlich | 604/298 |
| 4,531,944 | 7/1985 | Bechtle | 604/302 |
| 4,543,096 | 9/1985 | Keene | 604/300 |
| 4,605,398 | 8/1986 | Herrick | 604/300 |
| 4,685,906 | 8/1987 | Murphy | 604/300 |
| 4,733,802 | 3/1988 | Sheldon | 604/302 X |

*Primary Examiner*—Allen M. Ostrager
*Attorney, Agent, or Firm*—Blum Kaplan

[57] ABSTRACT

An occular treatment apparatus for applying liquid medicament from a reservoir is provided. The apparatus includes a tubular housing with a first open end adapted to conform to the shape of the facial area surrounding the eye socket. The housing is constructed and arranged to receive, hold and position a reservoir containing the liquid medicament. A sighting opening is included on the housing to properly orient the eye and distract the user from the drops of liquid medicament to be introduced into the eye. An eyelid displacement mechanism is supported on the first open end of the housing at a position diametrically opposed to the sighting opening. The displacement mechanism is adapted to evert the lower eyelid and expose the cul de sac. This combination of an eye focused at the sighting hole and an everted lower eyelid exposes the cul de sac so that drops of medicament dispensed into the eye will more easily and directly be applied at or near the cul de sac where it is temporarily retained to increase the length of time the medicament will medicate the eyeball. In a further embodiment of the instant invention, the lower eyelid displacement mechanism will simultaneously cause drops of to be emitted from the reservoir as the cul de sac is everted to facilitate application of the drops of liquid medicament.

19 Claims, 3 Drawing Sheets

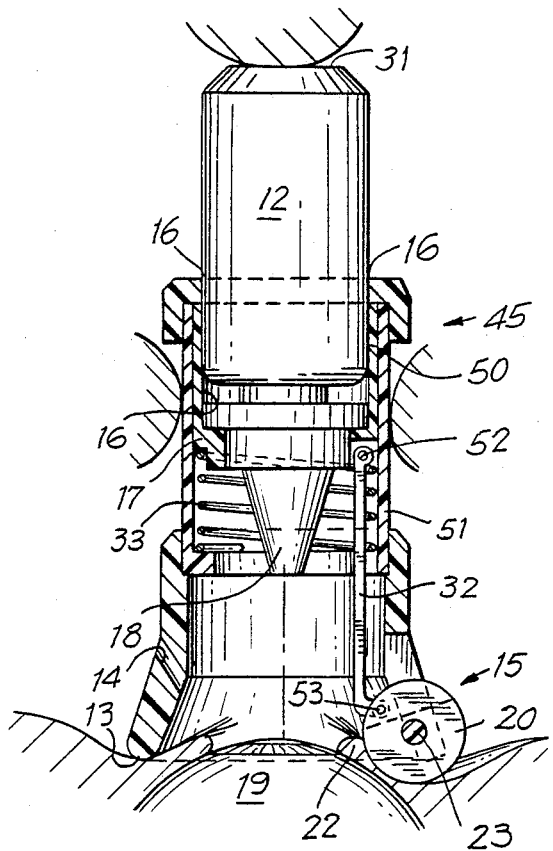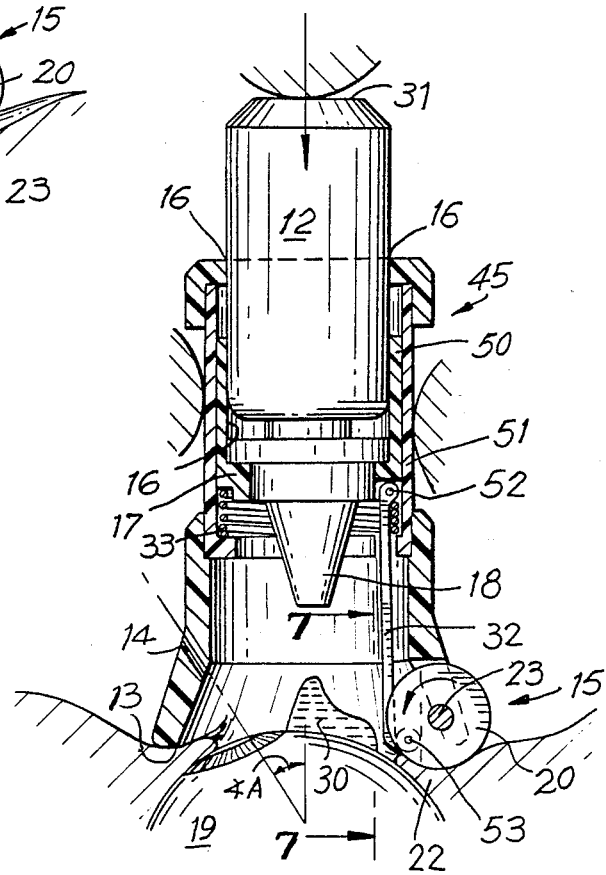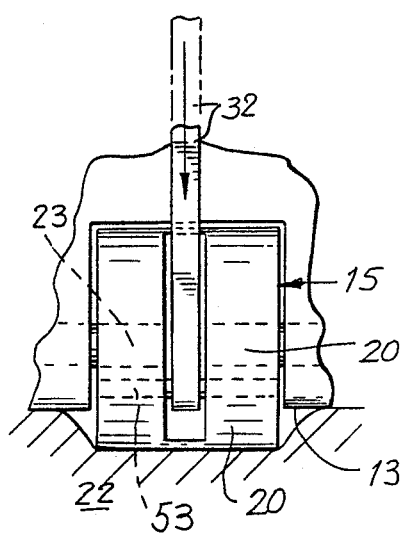

OCCULAR TREATMENT APPARATUS

BACKGROUND OF THE INVENTION

This invention is directed to an occular treatment apparatus and, in particular, to an occular treatment apparatus that can apply eye drops of liquid medicament safely and easily. Specifically, most people encounter difficulty in applying drops to their eyes. The eye is known to be a very sensitive body part and individuals find to difficult to control reflexive blinking when applying drops thereto. Also, eye drop users often have poor vision. Poor vision makes it difficult to position the tip of the dropper bottle over the eye and frequently causes drops to be incorrectly applied to the nose or cheek. Additionally, elderly people often have difficulty holding a dropper bottle steady or encounter difficulty in squeezing the bottle to apply a proper quantity of the medicament.

Even if the liquid medicament is properly applied to the cornea, the medicament's effectiveness is limited. The maximum volume of a drop of liquid medicament which can be introduced into contact with an eye at one time is about 30 microliters. Any amount that is greater usually spills over the eyelid onto the cheek. When eye drops are applied to the surface of the eyeball, blinking and natural tear flow combine to limit the time to a few minutes that liquid medicament will remain effective. However, if medicament is applied to the cul de sac of the conjunctiva, the medicament will remain effective for a longer period of time, maximizing the benefits of applying drops of liquid medicament to the eye.

U.S. Pat. No. 4,543,096 describes and illustrates an apparatus having finger-like projections which are attached to the front of an eye drop bottle to spread the eyelids apart during the eye drop dispensing process. One moveable finger is connected to a lever for depressing the lever and simultaneously causing the eyelids to spread apart while forcing a drop from the dropper bottle. However, the apparatus described in U.S. Pat. No. 4,543,069 will not properly steady the eyeball nor expose the cul de sac. Further, the finger-like projections could cause injury to the eye if a user accidentally contacts his cornea with one of the projections. Similarly, U.S. Pat. No. 4,531,944 depicts an appratus for steadying the tip of a dropper over the eye and further includes a sighting hole to distract the eye. However, this apparatus does not have a means to expose the cul de sac nor keep the lower eyelid depressed.

Accordingly, an occular treatment apparatus that is capable of simultaneously steadying the eyeball, orienting the application of the medicament, applying the medicament and exposing the cul de sac is desired.

SUMMARY OF THE INVENTION

Generally speaking, in accordance with the invention, an occular treatment apparatus is provided for applying liquid medicament from a reservoir. The apparatus includes a tubular housing with a first open end adapted to conform to the shape of the facial area surrounding the eye socket. The housing is constructed and arranged to receive, hold and position a reservoir containing the liquid medicament. A sighting opening is included on the housing to properly orient the eye and distract the user from the drops of liquid medicament to be introduced into the eye. An eyelid displacement mechanism is supported on the first open end of the housing at a position diametrically opposed to the sighting opening. The displacement mechanism is adapted to evert the lower eyelid and expose the cul de sac. This combination of an eye focused at the sighting hole and an everted lower eyelid exposes the cul de sac so that drops of medicament dispensed into the eye will more easily and directly be applied at or near the cul de sac where it is temporarily retained to increase the length of time the medicament will medicate the eyeball. In a further embodiment of the instant invention, the lower eyelid displacement mechanism will simultaneously cause drops of to be emitted from the reservoir as the cul de sac is everted to facilitate application of the drops of liquid medicament.

Accordingly, it is an object of this invention to provide an improved occular treatment apparatus for facilitating the application of drops of liquid medicament to the eye.

Another object of the invention is to provide an improved occular treatment apparatus capable of simultaneously displacing the lower eyelid and steadying and orienting the eyeball so that liquid medicament may be safely and easily applied.

A further object of the invention is to provide an improved occular treatment apparatus wherein the occular cul de sac is exposed during application of drops of liquid medicament.

Still another object of the invention is to provide an occular treatment apparatus which facilitates the orienting of a medicament reservoir over the eye, displaces the lower eyelid, and emits the liquid medicament from the reservoir.

Still other objects and advantages of the invention will in part be obvious and will in part be apparent from the specification and drawings.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 5 is a sectional view of an alternative embodiment of the occular treatment apparatus;

FIG. 6 is a sectional view illustrating the operation of the apparatus shown in FIG. 5; and FIG. 7 is a sectional view taken along line 7—7 of FIG. 6.

DETAILED DESCRIPTION OF THE PREFERRED EMBODIMENTS

Figure 1:
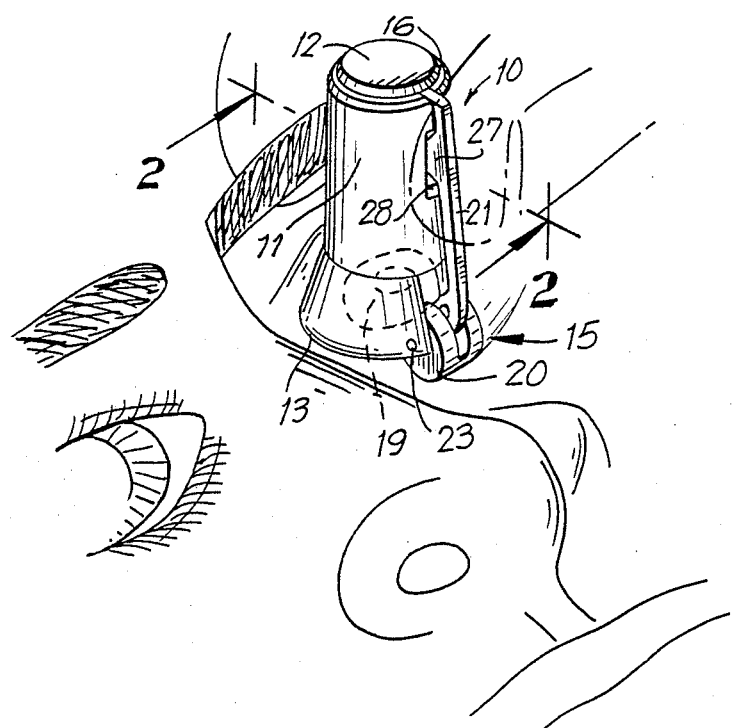
FIG. 1 is a perspective view of a preferred embodiment of the occular treatment apparatus.
Figure 2:
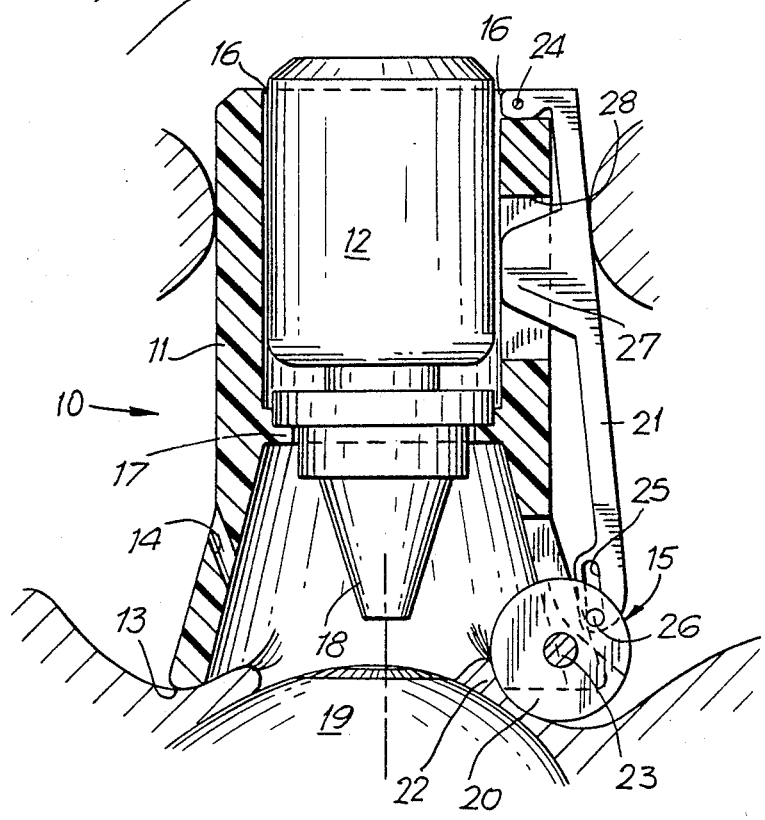
FIG. 2 is a sectional view taken along line 2—2 of FIG. 1.
Figure 3:
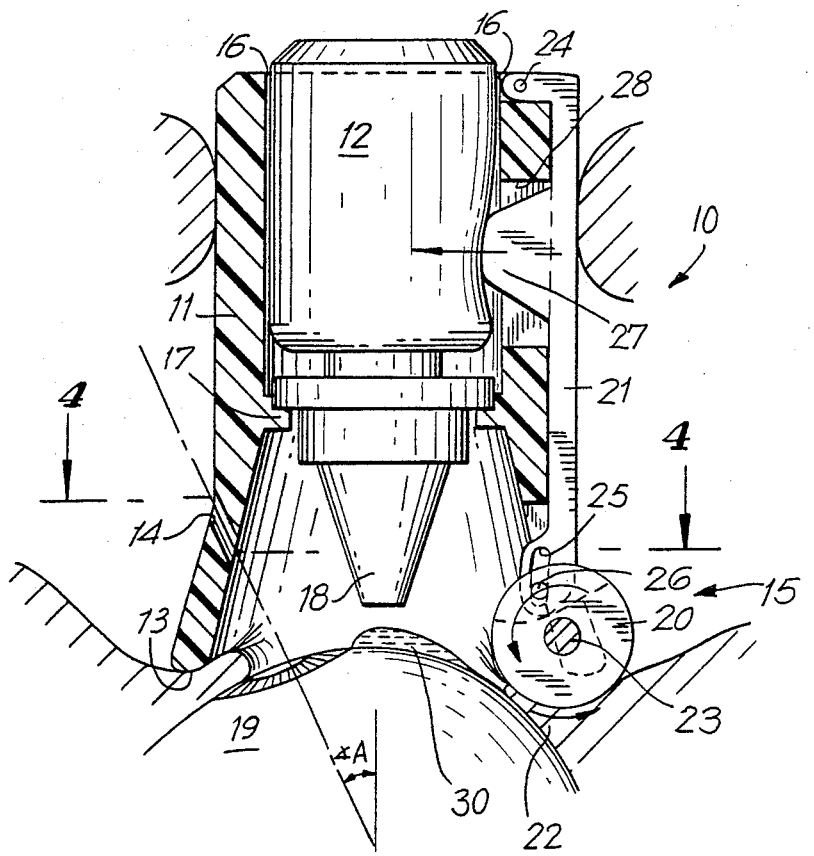
FIG. 3 is a sectional view taken along line 2—2 of FIG. 1 illustrating the operation of the occular treatment apparatus.
Figure 4:
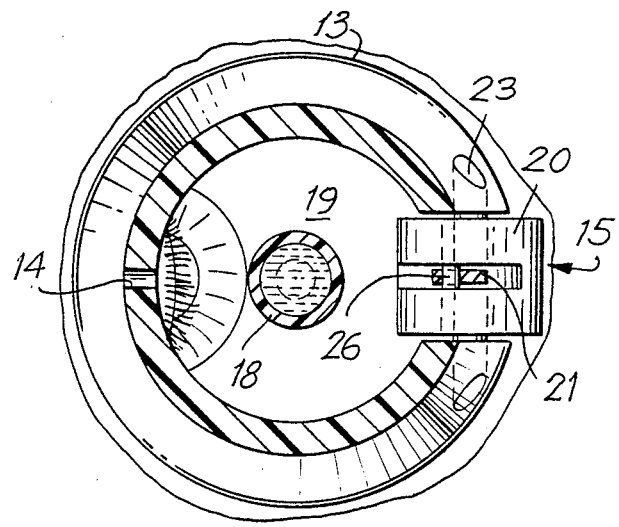
FIG. 4 is a sectional view taken along line 4—4 of FIG. 3.

Referring generally to FIGS. 1 to 4, a preferred embodiment of the occular treatment apparatus of the instant invention is indicated generally at 10. Apparatus 1 includes a tubular housing 11 constructed and arranged to receive and hold a dropper bottle 12. Housing 12 includes a front opening 13 which conforms to the facial area surrounding an eye 19. A sighting opening 14 is positioned in the tubular housing proximate to front opening 13 to properly orient an eyeball during use of the occular treatment apparatus. A displacement mechanism, illustrated generally at 15, is included on housing 11 at a position generally diametrically opposite sighting opening 14. Displacement mechanism 15 retracts the lower eyelid to expose a surface on the eye below the pupil for application of medicament from reservoir 12.

In an exemplary embodiment, housing 11 is constructed and arranged to retain a dropper bottle 12. However, the housing can be modified to hold a dropper, single dose dropper vial, pressurized propellant device or any other suitable applicator that stores and can deliver liquid medicament to the eye.

Accordingly, housing 11 includes a rear opening 16 shaped to receive dropper bottle 12. Housing 11 includes a radially disposed collar 17 for receiving and releasably securing the neck of dropper bottle 12. Housing 11 is configured so that the longitudinal axis of dropper bottle 12 is substantially parallel to and substantially aligned with the longitudinal axis of housing 11.

Front opening 13 is configured to nest in the facial area surrounding the eye socket. It is shaped so that apparatus 10 may be placed over the eye and easily maintained in a steady position with the tip of a dropper bottle nozzle 18 correctly positioned over eye 19. In this manner, when front opening 13 is positioned to surround the eye and a person tilts his head back the drop of medicament falling from nozzle 18 will fall into the eye 19 by gravity.

An eyelid displacement mechanism, located generally at 15, for safely and comfortably retracting the lower eyelid is included in the occular treatment apparatus. It is desirable for the medicament to flow to the interior cul de sac to extend the effectiveness of the medicament. Sliding the lower eyelid back and down helps to uncover the occular cul de sac which is a non-sensitive part of the conjunctiva. Displacement mechanism 15 includes an engagement body 20 and drive member 21. Engagement body 20 is a curved member which contacts lower eyelid 22 when front opening 13 is positioned around the eye. Engagement body 20 is rotatably mounted to housing 11 at front opening 13 by axle 23. When curved engagement body 20 is caused to partially rotate, it everts lower eyelid 22 and exposes the cul de sac.

The curved design of engagement body 20 provides several important benefits. The area of contact between the curved surface of engagement body 20 and lower eyelid 22 is considerable. This helps evert the eyelid properly and feels similar to using one's own finger to evert the eyelid. The wide engagement surface also makes exact placement of the engagement body 20 less critical. The curved surface of engagement body 20 also prevents injuries which can occur when an instrument for sliding the eyelids back is utilized.

To utilize apparatus 10, front opening end 13 is placed over the eye with engagement body 20 resting against lower eyelid 22. As depicted generally in FIG. 3, an elongated drive shaft 21 is then displaced to partially rotate engagement body 20. A first end of drive shaft 21 is pivotally connected to housing 11 by pivot pin 24. A second end of drive shaft 21 is pivotally and slideably connected to engagement body 20 at slot 25, which is positioned around drive pin 26. Drive shaft 21 includes a projection 27 intermediate its first and second ends. Housing 11 includes a housing slot 28 through rear opening 16 aligned with projection 27 so that when drive shaft 21 is moved towards housing 11, projection 27 will pass through housing slot 28 to compress dropper bottle 12 and force drops 30 of liquid medicament from nozzle 18. As drive shaft 21 moves towards housing 11, the sides of slot 25 push against drive pin 26 to partially rotate engagement body 20 to retract lower eyelid 22 coincident with liquid 30 being introduced to the eye from nozzle 18.

Sighting opening 14 is positioned proximate front open end 13 to correctly orient the eye and help uncover the cul de sac. It also helps control reflexive blinking which is often caused by the user sensing something approaching his exposed eye. Sighting opening 14 is provided in housing 11 near front opening 13 at a position diametrically opposed to curved engagement body 20 so that a user will have his eye steadied in an upwardly rotated position when his lower eyelid is everted. To properly uncover the cul de sac, sighting opening 14 should be positioned near front opening 13 so that the eye will be oriented upwardly through an angle A which should be at least 30°. However, a in a preferred embodiment angle A is greater than 35°. Because the only light perceived by the user passes through sighting hole 14, a person having poor vision is assisted in properly orienting their eyeball.

Referring next to FIGS. 5 through 7, a further embodiment of the occular treatment apparatus, generally indicated as 45 is depicted, like reference numerals being utilized to depict like elements discussed above. This embodiment has the same curved engagement body 20, front opening 13, sighting hole 14 and collar 17. However, the mechanism for rotating engagement body 20 is structurally distinct. Bottle 12 rests in slidable seat 50. Seat 50 can slide within outside tubular housing 51 and is upwardly biased by spring 33. Vertical drive shaft 32 has two ends. Its first end is pivotably connected to slideable seat 50 by pin 52. The second end of vertical drive member 32 is slideably and pivotably connected to curved engagement body 20, by drive pin 53. When bottle 12 is inserted into the housing to compress spring 33, vertical drive shaft 32 causes curved engagement bdy 20 to partially rotate, everting lower eyelid 22.

Specifically, a user places front opening 13 of apparatus 45 over the eye and contacts the lower eyelid with engagement body 20. To dispense drops of liquid medicament, the user again peers through sighting opening 14. To evert the lower eyelid, end 31 of dropper bottle 12 is poushed into the housing, causing vertical drive member 32 to rotate curved engagement body 20.

Accordingly, this further embodiment causes the force necessary to evert the lower eyelid to be applied in a direction which will increase the contacting pressure between engagement body 20 and lower eyelid 22. This will decrease the chance of slippage to insure that lower eyelid 22 is everted. Spring 33 returns the apparatus to its original position shown in FIG. 5.

Accordingly, when the occular treatment apparatus of the instant invention is used to apply liquid medicament to the eye, the above indicated advantages are observed. The dropper bottle is steadied over the eye in a correct orientation; the cul de sac of the conjunctiva is exposed by the combination of orienting the eyeball in an upwardly gazing position while everting the lower eyelid; involuntary blinking is prevented by the user focusing on light passing through the sighting opening at the same time that the lower eyelid is held in a depressed position. Therefore, drops of liquid medicament can be applied to the eye so that the medicament will flow to the cul de sac to increase the half life of its effectiveness.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. An occular treatment apparatus for applying liquid medicament from a reservoir comprising: a tubular housing with a first open end adapted to conform to the shape of the facial area surrounding the eye socket, said housing being constructed and arranged to receive a reservoir of liquid medicament, said housing including sighting means for orienting an eye, and displacement means supported by said housing proximate said first open end at a position diametrically opposed to said sighting means, said displacement means being adapted to evert a lower eyelid so that liquid medicament from the reservoir is easily and safely applied to the occular cul de sac.

2. The occular treatment apparatus, as claimed in claim 1, wherein said displacement means includes an engagement body, rotatably connected to said housing proximate said first open end, said engagement body adapted to engage the lower eyelid and evert the lower eyelid when said engagement body is rotatably displaced.

3. The occular treatment apparatus, as claimed in claim 2, wherein said displacement means further includes rotation drive means, which will cause said engagement body to be rotatably displaced when the rotation drive means is activated.

4. The occular treatment apparatus, as claimed in claim 3, wherein said rotation drive means includes a drive shaft with a first end and a second end, said first end pivotally connected to said housing and said second end pivotally and slideably connected to said engagement body in a manner so that pivoting the member about the pivotable connection at first end will cause the curved body to be rotatably displaced.

5. The occular treatment apparatus, as claimed in claim 3, wherein said rotation drive means is constructed and arranged so that activating said rotation drive means will simultaneously rotatably drive the engagement body while causing liquid medicament to be emitted from a reservoir.

6. The occular treatment apparatus, as claimed in claim 2, and including said housing having an aperture through the portion of the housing where a reservoir is received, wherein the displacement means includes a drive shaft having a first end and a second end and a projection therebetween, said projection sized to pass through the aperture to compress a reservoir when it passes through the aperture, said first end of the drive shaft pivotally connected to the housing and said second end of the drive shaft pivotally and slideably connected to the engagement body in a manner to rotatably displace the engagement body when the drive shaft is pivotted about said first end of the drive shat, said the drive shaft positioned on said housing to allow the projection on the drive shaft to pass through the aperture and the projection is positioned on the drive shaft so that when the drive shaft is pivotted about said first end of the drive shaft to rotatably dsiplace the engagement body, the projection will pass through the aperture to compress a reservoir and cause liquid medicament to be emitted from a reservoir.

7. The occular treatment apparatus, as claimed in claim 1, wherein said sighting means includes the portion of the housing proximate the first open end defining an aperture.

8. The occular treatment apparatus, as claimed in claim 1, wherein said sighting means includes the portion of the housing proximate the first open end defining an aperture shaped and positioned to cause a user to rotate their eye more than about 30° upwards to peer at light passing through the aperture.

9. The occular treatment apparatus, as claimed in claim 2, wherein said sighting means is positioned to cause a user to rotate their eye more than about 30° upwards from its normal position to peer at the sighting means.

10. The occular treatment apparatus, as claimed in claim 2, wherein said sighting means is positioned to cause a user to rotate their eye more than about 35° upwards from its normal position to peer at the sighting means.

11. The occular treatment apparatus, as claimed in claim 2, wherein the surface of the portion of said engagement body which engages the lower eyelid is curved.

12. The occular treatment apparatus for applying liquid medicament from a reservoir comprising: a tubular housing with a first open end adapted to conform to the shape of the facial area surrounding the eye socket, said housing being constructed and arranged to receive a reservoir of liquid medicament, said housing including sighting means for orienting an eye, and displacement means supported by said housing proximate said first open end at a position diametrically opposed to said sighting means, said displacement means being adapted to engage a lower eyelid and coincidentally displace said lower eyelid down and back to uncover the portion of the eye below the pupil while liquid medicament is safely and easily applied to that portion of the eye.

13. The occular treatment apparatus, as claimed in claim 12, wherein said sighting means is positioned to cause a user to rotate their eye more than about 30° upwards from its normal position to peer at the sighting means.

14. The occular treatment apparatus, as claimed in claim 12, wherein said sighting means includes said first open portion of the housing defining an aperture.

15. The occular treatment apparatus, as claimed in claim 14, wherein the first open portion defining the aperture is positioned and shaped to cause a user to rotate their eye more than about 30° upwards from its normal position to peer at light passing through the aperture.

16. The occular treatment apparatus, as claimed in claim 12, wherein said displacement means includes an engagement body, rotatably connected to said housing proximate said first open end, said engagement body adapted to engage the lower eyelid and displace the eyelid down and back when said engagement body is rotatably displaced.

17. The occular treatment apparatus, as claimed in claim 16, wherein said displacement means further includes a rotation drive means which will rotate the engagement body when the rotation drive mean is activated.

18. The occular treatment apparatus, as claimed in claim 16, and including said housing having an aperture through the portion of the housing adjacent where a reservoir is placed wherein the displacement means includes a rotation drive shaft having a first end and a second end and a projection therebetween, said projection sized to pass through the aperture to compress a reservoir, said first end of the drive shaft pivotally connected to the housing and said second end of the drive shaft pivotally and slideably connected to the engagement body in a manner which will rotatably dislace the engagement body when the drive shaft is pivoted about said first end of the drive shaft, the drive shaft positioned on the housing to allow said projection on the drive shaft to pass through the aperture and the projection is positioned on the drive shaft so that when the drive shaft is pivoted about said first end to rotatably displace the engagement body, the projection will pass through the aperture to compress a reservoir and cause liquid medicament to be emitted from a reservoir.

19. The occular treatment apparatus, as claimed in claim 18, wherein said sighting means includes said front open portion of the housing defining an aperture.

* * * * *